United States Patent [19]

Wade et al.

[11] 4,147,698
[45] Apr. 3, 1979

[54] 3-(HETEROCYCLICALKYLAMINO)BENZISOTHIAZOLE-1,1-DIOXIDES

[75] Inventors: Peter C. Wade, Pennington, N.J.; B. Richard Vogt, Yardley, Pa.

[73] Assignee: E. R. Squibb & Sons, Inc., Princeton, N.J.

[21] Appl. No.: 924,340

[22] Filed: Jul. 13, 1978

[51] Int. Cl.² .................. C07D 275/06; A61K 31/425
[52] U.S. Cl. .................................... 260/301; 424/270
[58] Field of Search ........................... 260/301, 304 A

[56] References Cited
U.S. PATENT DOCUMENTS

| 2,751,392 | 6/1956 | Grogan | 260/301 |
| 3,225,056 | 12/1965 | Traverso | 260/301 |
| 3,271,406 | 9/1966 | Traverso | 260/301 |
| 3,457,272 | 7/1969 | Crook | 260/301 |

Primary Examiner—Paul M. Coughlan, Jr.
Assistant Examiner—Lisa Jones
Attorney, Agent, or Firm—Lawrence S. Levinson; Merle J. Smith; Donald J. Barrack

[57] ABSTRACT

Compounds having the formula

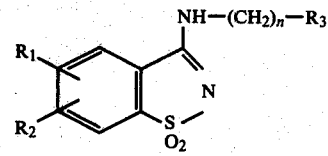

wherein $R_1$ is hydrogen, halogen, alkyl alkoxy or nitro; $R_2$ is hydrogen, halogen or alkoxy; $R_3$ is an imidazol-4-yl or indol-3-yl; and n is 1,2,3 or 4, have antiinflammatory activity.

6 Claims, No Drawings

3-(HETEROCYCLICALKYLAMINO)BENZISO-THIAZOLE-1,1-DIOXIDES

RELATED APPLICATIONS

United States patent application Ser. No. 799,865, filed May 23, 1977, now U.S. Pat. No. 4,104,387, by Wade and Kissick, discloses 3-(arylcycloiminoalkyloxy)-benzisothiazole, 1,1-dioxides and 3-(arylcycloiminoalkylamino)benzisothiazole 1,1-dioxides having antiinflammatory activity.

United States patent application Ser. No. 799,879 filed May 23, 1977, now U.S. Pat. No. 4,104,388, by Wade and Kissick, discloses 3-(cycloimino)benzisothiazole 1,1-dioxides, 3-(hydroxycycloimino)benzisothiazole 1,1-dioxides and 3-(arylcycloimino)benzisothiazole 1,1-dioxides having antiinflammatory activity.

United States patent application Ser. No. 875,022, filed Feb. 3, 1978 by Wade and Vogt, discloses [(1,1-dioxo-1,2-benzisothiazol-3-yl)amino] alkanoic acids and esters thereof, and [(1,1-dioxo-1,2-benzisothiazol-3-yl)amino]-cycloalkanoic acids and esters thereof, having antiinflammatory activity.

United States patent application Ser. No. 875,021, filed Feb. 3, 1978 by Wade, Vogt and Kissick, discloses 2,3-dihydro-1,2,4-triazolo [4,3-b][1,2]benzisothiazol-3-amine, 5,5-dioxides having antiinflammatory activity.

United States patent application Ser. No. 875,020, filed Feb. 3, 1978 by Wade and Kissick, discloses 3-(substituted hydrazino)benzisothiazole 1,1-dioxides having the formulas

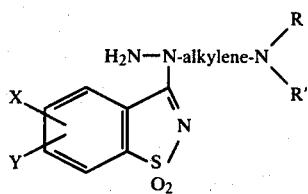

and

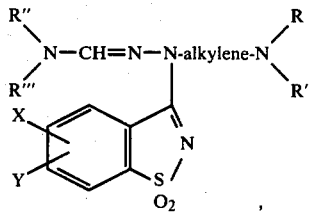

wherein X is hydrogen, halogen, alkyl, alkoxy or nitro, Y is hydrogen, halogen, or alkoxy and each of the —NRR groups is dialkylamino or a 5- or 6-membered heterocycle. The compounds have antiinflammatory activity.

United States patent application Ser. No. 875,018, filed Feb. 3, 1978, now U.S. Pat. No. 4,108,860, by Wade, Vogt and Kissick, discloses 1,2,4-triazolo-[4,3-b][1,2]benzisothiazole, 5,5-dioxides and 3-aryl and 3-alkyl derivates having antiinflammatory activity.

BACKGROUND OF THE INVENTION

U.S. Pat. No. 2,751,392, issued June 19, 1956, discloses, inter alia, compounds having the formula

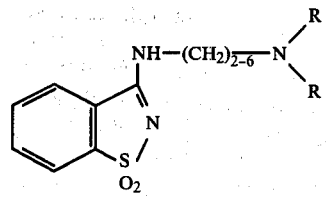

wherein R is alkyl or the —NRR grouping can be a heterocyclic ring. The compounds are said to have analgesic and antihistaminic activity.

U.S. Pat. No. 3,225,056, issued Dec. 21, 1965, discloses, inter alia, 3-(substituted hydrazino)benzisothiazoles having the formula

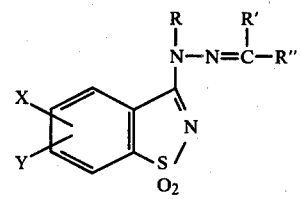

wherein X and Y are hydrogen, halogen, alkyl, alkoxy or trifluoromethyl; R and R' when taken alone are hydrogen; R" when taken alone is alkyl or alkenyl; R' and R" taken together with the carbon atom to which they are attached form a cyclopentyl or cyclohexyl ring; and R and R' when taken together with the

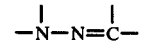

grouping to which they are attached form a heterocyclic ring. The above compounds are said to have hypotensive and diuretic activity.

U.S. Pat. No. 3,271,406 issued Sept. 4, 1966, discloses 3-(substituted hydrazino) benzothiazoles having the formula

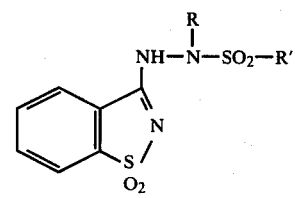

wherein R is hydrogen, alkyl or alkenyl and R' is alkyl, phenyl, α-naphthyl or β-naphthyl. The compounds are said to have hypotensive activity.

U.S. Pat. No. 3,457,272, issued July 22, 1969, discloses, inter alia, N-substituted-1,2-benzisothiazole-3-one, 1,1-dioxides. The compounds are said to exhibit various central nervous system activities.

BRIEF DESCRIPTION OF THE INVENTION

Compounds having the formula

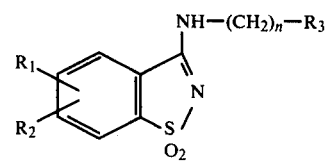

I and the pharmaceutically acceptable salts thereof, have antiinflammatory activity. In formula I, and throughout the specification, the symbols are as defined below.

$R_1$ is hydrogen, halogen, alkyl, alkoxy or nitro and $R_2$ is hydrogen, halogen or alkoxy, with the proviso that if $R_2$ is other than hydrogen, $R_1$ and $R_2$ are the same;

$R_3$ is

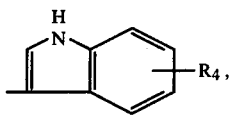 (i)

wherein $R_4$ is hydrogen, halogen, alkyl, alkoxy or nitro, or

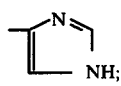 (ii)

and n is 1,2,3 or 4(2 and 3 are preferred).

The terms "alkyl" and "alkoxy," as used throughout the specification, refer to groups having 1 to 4 carbon atoms; groups having 1 or 2 carbon atoms are preferred.

The term "halogen," as used throughout the specification, refers to fluorine, chlorine, bromine and iodine; chlorine and bromine are preferred.

DETAILED DESCRIPTION OF THE INVENTION

The compounds of formula I can be prepared by reacting a 3-halo-1,2-benzisothiazole, 1,1-dioxide having the formula

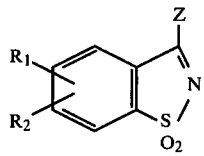 II wherein Z is halogen (chlorine being the most preferred) with a primary amine having the formula

III

The reaction can be run in an organic solvent, e.g., dioxane, benzene, dimethylformamide, dimethoxyethane or the like.

The starting materials of formula III are known in the art. Some of the starting materials are commercially available and all of them are readily obtainable via conventional synthetic routes.

The 3-halo-1,2-benzisothiazole, 1,1-dioxides of formula II are also known in the art; see, for example, U.S. Pat. No. 3,225,056, issued Dec. 12, 1965. They can be prepared from the corresponding saccharin compound having the formula

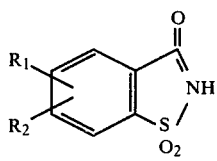 IV by reaction with thionyl chloride in an inert organic solvent, preferably with a catalytic amount of dimethylformamide.

The pharmaceutically acceptable salts of the compounds of formula I can be prepared from the corresponding free base using procedures well known in the art. Acid-addition salts are specifically contemplated, e.g., the hydrohalides (particularly the hydrochloride and hydrobromide), sulfate, nitrate, phosphate, tartrate, maleate, fumarate, citrate, succinate, methanesulfonate, benzenesulfonate, toluenesulfonate and the like.

The compounds of formula I, and the pharmaceutically acceptable salts thereof, can be used to treat inflammation in mammals. Joint tenderness and stiffness (in conditions such as rheumatoid arthritis) can be reduced by these compounds.

The compounds of this invention can be formulated for use as antiinflammatory agents according to accepted pharmaceutical practice in oral dosage forms such as tablets, capsules, elixirs or powders, or in an injectable form in a sterile aqueous vehicle. The compounds of this invention can be administered in amounts of 100 milligrams per kilogram of animal body weight per day to 2 grams per kilogram of animal body weight per day, preferably 100 milligrams per kilogram of animal body weight per day to 1 gram per kilogram of animal body weight per day.

The following examples are specific embodiments of this invention.

EXAMPLE 1

N-[2-(1H-Indol-3-yl)ethyl]-1,2-benzisothiazol-3-amine, 1,1-dioxide

Tryptamine hydrochloride (10.46 g) is converted to its free base using chloroform and aqueous sodium hydroxide. The free base and 8.0 g. of 3-chloro-1,2-benzisothiazole, 1,1-dioxide are refluxed in 100 ml. of dioxane for 30 minutes and then stirred for about 16 hours at room temperature. A precipitate (tryptamine hydrochloride) is filtered off.

The dioxane filtrate is evaporated and the solid residue is washed as a slurry with 10% hydrochloric acid, water and 5% sodium hydroxide, collected on a filter and washed with water. The filter cake is dissolved in a mixture of 5 ml. of dimethylformamide-100 ml. of ethanol and crystallized out by adding 100 ml. of water. The material is dissolved in a hot solution of 2 ml dimethylformamide-300 ml ethanol and 50 ml of water, stirred with 2 g of charcoal for 5 minutes and filtered through diatomaceous earth. After adding 300 ml of water to the filtrate, the product crystallizes out, is filtered off, washed with water and dried at 70° C., in vacuo, yielding 4.25 g of the title compound, melting point 203°–205° C.

EXAMPLE 2

N-[2-(1H-Imidazol-4-yl)ethyl]-1,2-benzisothiazol-3-amine, 1,1-dioxide and the hydrochloride salt thereof Histamine dihydrochloride (7.31 g.) is exactly neutralized by dissolution in 79.4 ml. of 1N sodium hydroxide. The water is evaporated under vacuum and the residue is stirred in 25 ml. of dimethylformamide. 3-Chloro-1,2-benzisothiazole, 1,1-dioxide (8.0 g), in 100 ml of dioxane is added dropwise over a period of 10 minutes at room temperature. The reaction mixture is stirred for 10 minutes and then filtered. The solvent is removed from the filtrate, in vacuo, and the residue is taken up in a mixture of benzene, water and triethylamine. After shaking for 4 hours N-[2-(1H-imidazol-4-yl)ethyl]-1,2-benzisothiazol-3-amine, 1,1-dioxide is filtered from the two liquid phases, washed in a funnel with water and dried at 60° C. (1 mm of Hg) for 4 hours, yielding 3.2 g of the free base product, melting point 130°-140° C.

The above free base is dissolved in ethanolic hydrogen chloride and the hydrochloride salt is precipitated out by the addition of ether. The hydrochloride salt is filtered off and dried at 80° C. (1 mm of Hg) for 4 hours to yield 1.3 g of N-[2-(1H-imidazol-4-yl)ethyl]-1,2-benzisothiazol-3-amine, 1,1-dioxide, hydrochloride (1:1), melting point 222°-224° C.

The original filter cake is taken up in a mixture of benzene, water and triethylamine and shaken for 4 hours. N-[2-(1H-Imidazol-4-yl)ethyl]-1,2-benzisothiazol-3-amine, 1,1-dioxide is filtered from the two liquid phases, washed in the funnel with water and dried at 60° C. (1 mm of Hg) for 4 hours to yield 5.8 g of the free base product, melting point 143°-145° C.

EXAMPLES 3-10

Following the procedure of Example 1, but substituting the compound listed in column I for the free base of tryptamine hydrochloride and the compound listed in column II for 3-chloro-1,2-benzisothiazole,1,1-dioxide, yields the compound listed in column III.

|   | Column I | Column II | Column III |
|---|---|---|---|
| (3) | 3-(aminomethyl)-5-chloroindole | 3,5,6-trichloro-1,2-benzisothiazole, 1,1-dioxide | N-[(5-chloro-1H-indol-3-yl)methyl]-5,6-dichloro-1,2-benzisothiazol-3-amine, 1,1-dioxide |
| (4) | 3-(3-aminopropyl)-5-methylindole | 3-chloro-5-methyl-1,2-benzisothiazole, 1,1-dioxide | N-[3-(5-methyl-1H-indol-3-yl)propyl]-5-methyl-1,2-benzisothiazol-3-amine, 1,1-dioxide |
| (5) | 3-(4-aminobutyl)-5-methoxyindole | 3-chloro-5,6-dimethoxy-1,2-benzisothiazole, 1,1-dioxide | N-[4-(5-methoxy-1H-indol-3-yl)butyl]-5,6-dimethoxy-1,2-benzisothiazol-3-amine, 1,1-dioxide |
| (6) | tryptamine | 3-chloro-5-nitro-1,2-benzisothiazole, 1,1-dioxide | N-[2-(1H-indol-3-yl)ethyl]-5-nitro-1,2-benzisothiazol-3-amine, 1,1-dioxide |
| (7) | (4-imidazolyl)methylamine | 3,5-dichloro-1,2-benzisothiazole, 1,1-dioxide | 5-chloro-N-[1H-imidazol-4-yl)methyl]-1,2-benzisothiazol-3-amine, 1,1-dioxide |
| (8) | 3-(4-imidazolyl)propylamine | 3-chloro-5-methyl-1,2-benzisothiazole, 1,1-dioxide | N-[3-(1H-imidazol-4-yl)propyl]-5-methyl-1,2-benzisothiazol-3-amine, 1,1-dioxide |
| (9) | 4-(4-imidazolyl)butylamine | 3-chloro-5-methoxy-1,2-benzisothiazole, 1,1-dioxide | N-[4-(1H-imidazol-4-yl)butyl]-5-methoxy-1,2-benzisothiazol-3-amine, 1,1-dioxide |
| (10) | histamine | 3-chloro-5-nitro-1,2-benzisothiazole, 1,1-dioxide | N-[2-(1H-imidazol-4-yl)ethyl]-5-nitro 1,2-benzisothiazol-3-amine, 1,1-dioxide |

What is claimed is:

1. A compound having the formula

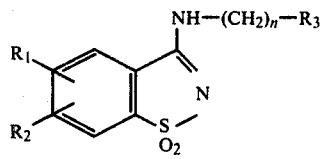

or a pharmaceutically acceptable salt thereof, wherein:

R$_1$ is hydrogen, halogen, alkyl, alkoxy or nitro and R$_2$ is hydrogen, halogen or alkoxy, provided that if R$_2$ is other than hydrogen, R$_1$ and R$_2$ are the same; R$_3$ is

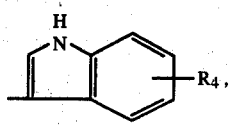

wherein R$_4$ is hydrogen, halogen, alkyl, alkoxy or nitro, or

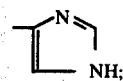

and n is 1,2,3 or 4.

2. A compound in accordance with claim 1 wherein R$_3$ is

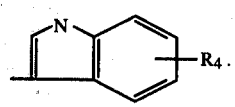

3. A compound in accordance with claim 1 wherein R$_3$ is

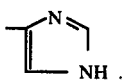

4. The compound in accordance with claim 1 having the name N-[2-(1H-indol-3-yl)ethyl]-1,2-benzisothiazol-3-amine, 1,1-dioxide.

5. The compound in accordance with claim 1 having the name N-[2-(1H-imidazol-4-yl)ethyl]-1,2-benzisothiazol-3-amine, 1,1-dioxide.

6. The compound in accordance with claim 1 having the name N-[2-(1H-imidazol-4-yl)ethyl]-1,2-benzisothiazol-3-amine, 1,1-dioxide, hydrochloride (1:1).

* * * * *